(12) United States Patent
Monetti

(10) Patent No.: US 7,048,719 B1
(45) Date of Patent: May 23, 2006

(54) ENDOVASCULAR CATHETER RESHEATHING APPARATUS AND RELATED METHODS

(75) Inventor: Richard R. Monetti, San Clemente, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 438 days.

(21) Appl. No.: 10/165,103

(22) Filed: Jun. 7, 2002

(51) Int. Cl.
*A61M 5/00* (2006.01)

(52) U.S. Cl. .................................... 604/171
(58) Field of Classification Search ............... 604/163, 604/171, 164.05
See application file for complete search history.

(56) References Cited

U.S. PATENT DOCUMENTS

| | | | |
|---|---|---|---|
| 3,225,762 A | 12/1965 | Guttman | |
| 3,537,451 A | 11/1970 | Beck et al. | |
| 3,559,643 A * | 2/1971 | Pannier et al. ............... | 604/171 |
| 3,570,485 A | 3/1971 | Reilly | |
| 3,742,958 A | 7/1973 | Rundles | |
| 3,769,975 A | 11/1973 | Nimoy et al. | |
| 3,853,130 A * | 12/1974 | Sheridan ..................... | 604/171 |
| 3,877,429 A | 4/1975 | Rasumoff | |
| 4,306,562 A | 12/1981 | Osborne | |
| 4,402,685 A | 9/1983 | Buhler et al. | |
| 4,412,832 A | 11/1983 | Kling et al. | |
| 4,449,973 A | 5/1984 | Luther | |
| 4,840,613 A * | 6/1989 | Balbierz ..................... | 604/533 |
| 4,887,997 A * | 12/1989 | Okada ........................ | 604/516 |
| 4,932,946 A | 6/1990 | Shields | |
| 4,988,356 A * | 1/1991 | Crittenden et al. .......... | 606/192 |
| 5,011,488 A | 4/1991 | Ginsburg | |
| 5,234,411 A * | 8/1993 | Vaillancourt ................ | 604/171 |
| 5,250,033 A | 10/1993 | Evans et al. | |
| 5,279,590 A | 1/1994 | Sinko et al. | |
| 5,489,273 A | 2/1996 | Whitney et al. | |
| 6,015,424 A | 1/2000 | Rosenbluth et al. | |
| 6,165,193 A | 12/2000 | Greene, Jr. et al. | |
| 6,193,691 B1 | 2/2001 | Beardsley | |
| 6,299,619 B1 | 10/2001 | Greene, Jr. et al. | |
| 6,447,540 B1 | 9/2002 | Fontaine et al. | |

* cited by examiner

*Primary Examiner*—Sharon Kennedy
(74) *Attorney, Agent, or Firm*—Robert D. Buyan; Stout, Uxa, Buyan & Mullins, LLP

(57) ABSTRACT

A resheathing apparatus for a tube that is insertable through an endovascular catheter includes a guide that has a proximal end, a distal end, at least one lumen extending from the proximal end to the distal end, and a branch extending away from the lumen at one end of the guide. A sheath may be placed over the tube by sliding the resheathing apparatus along the length of the tube. The resheathing apparatus may also include a guide tube that fits over the branch of the guide and directs a sheath over the tube that is insertable through an endovascular catheter. The resheathing apparatus may be used with vascular embolization devices, and may be used with devices that are delivered via microcatheter systems. Methods of using the resheathing apparatus are also disclosed.

2 Claims, 3 Drawing Sheets

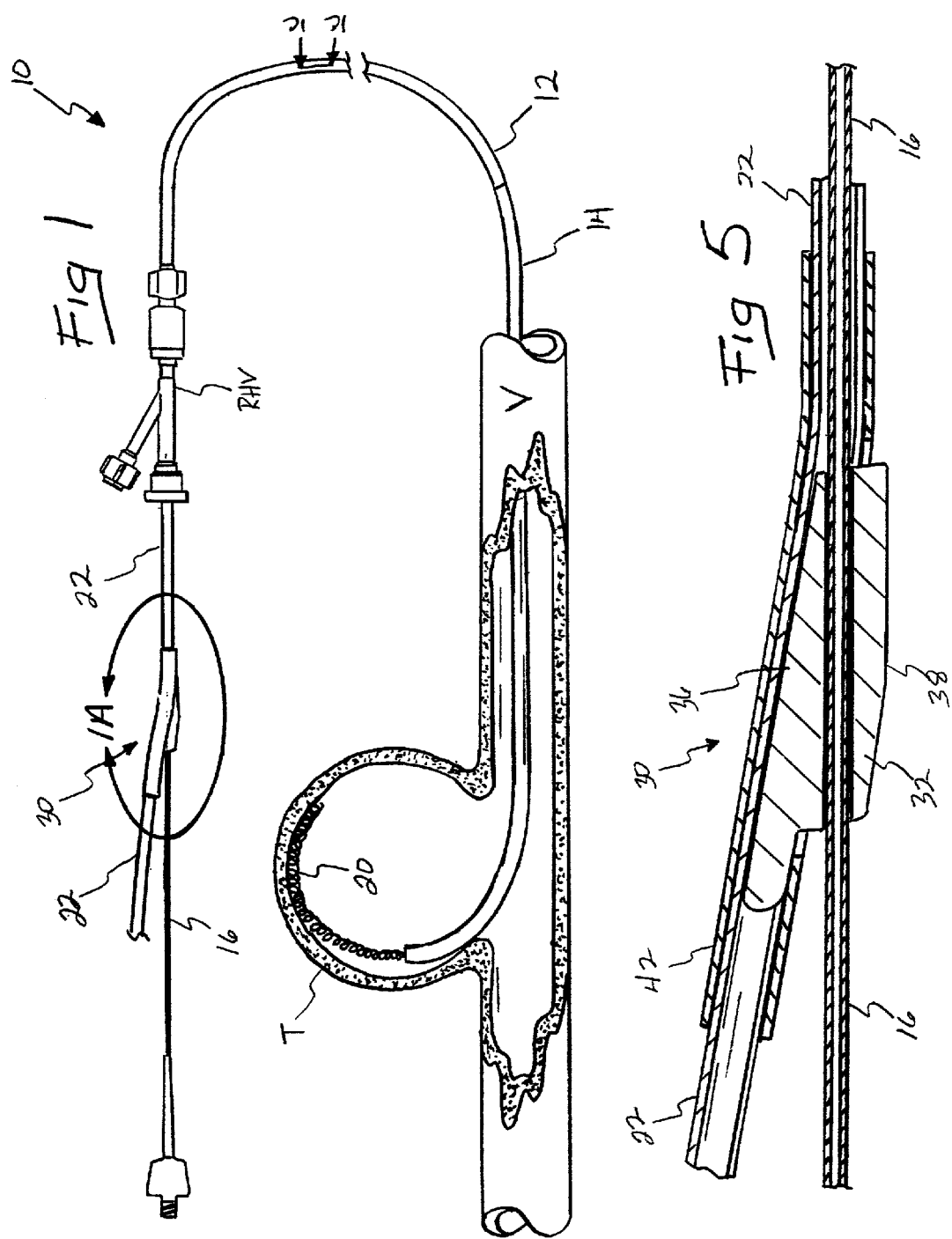

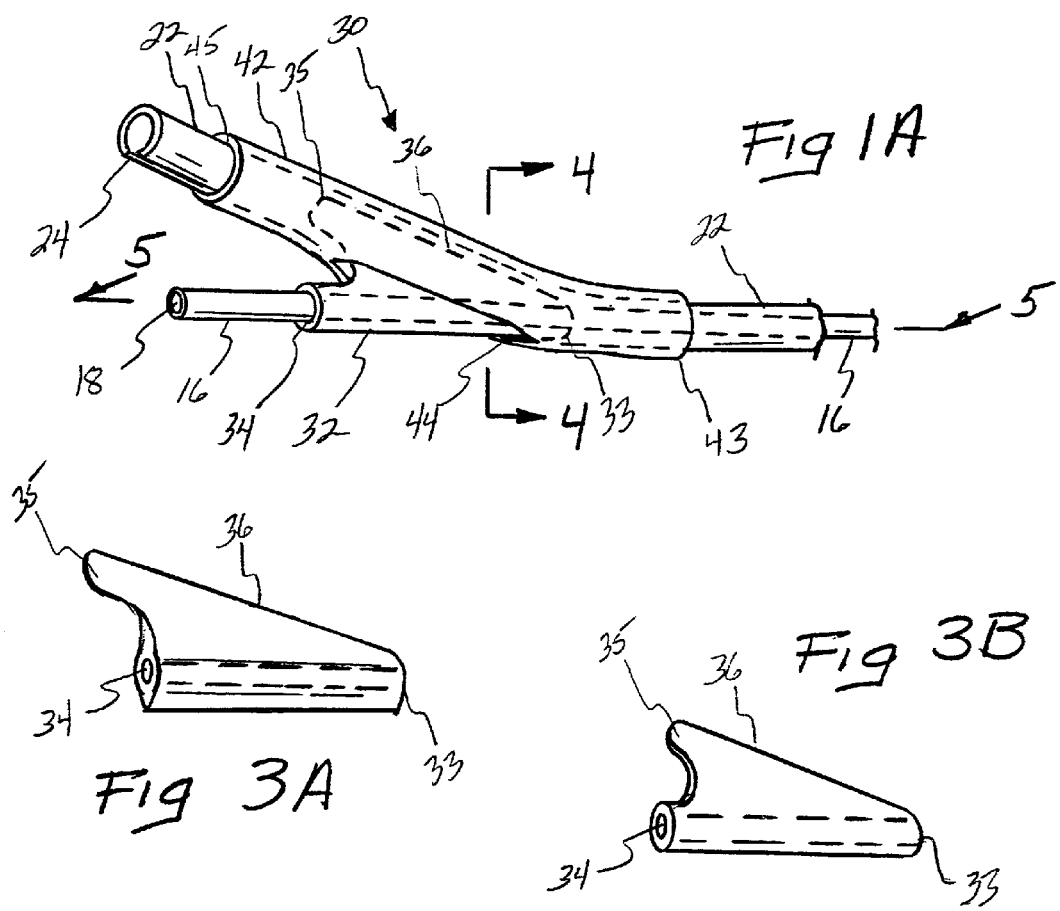
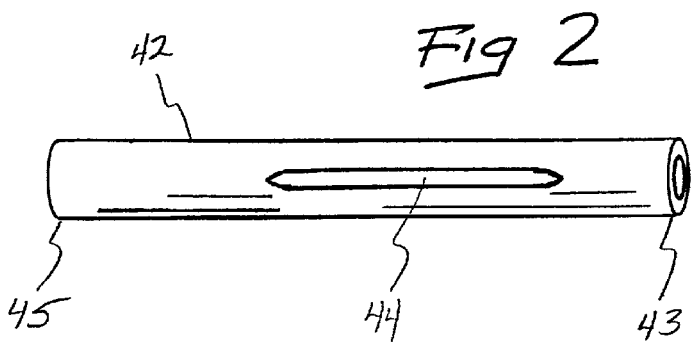

ENDOVASCULAR CATHETER RESHEATHING APPARATUS AND RELATED METHODS

FIELD OF THE INVENTION

This invention relates generally to medical devices and methods of using same. More particularly, the invention relates to apparatus and methods for resheathing devices that may be inserted into endovascular catheters, such as endovascular microcatheters.

BACKGROUND OF THE INVENTION

Endovascular catheters are commonly used to permit internal treatment of patients suffering from vascular disorders. For example, catheters may be used for angioplasty, and may be used to deliver embolic devices useful in occluding blood flow through a patient's vasculature. Blood flow occlusion may be useful in controlling vascular bleeding, controlling blood supply to tumors, and to occlude vascular aneurysms, including intracranial aneurysms. When treating blood vessels of extremely small size, for example, intracranial blood vessels, microcatheters may be employed.

Cerebral aneurysms and other vascular defects may sometimes be treated by delivering one or more embolic members (e.g., small coils) through a microcatheter positioned at, or near, the aneurysm or vascular defect. The embolic members are typically attached to an elongate deployment apparatus that is advanceable out of the distal end of the microcatheter and then releases the embolic member(s) into or near the aneurysm or vascular defect. The deployment apparatus is typically flexible enough to be advanced through blood vessels with minimal trauma to the damage to the blood vessels. To improve the advancement of the deployment apparatus, and to protect the deployment apparatus and the accompanying embolization member(s), the deployment apparatus and the accompanying embolization member(s) may be initially positioned within the lumen of a more rigid sheath. Such sheath is typically removed and discarded as the deployment apparatus and the accompanying embolization member(s) are advanced into the microcatheter. The sheath is flexible enough to permit the deployment apparatus to bend and follow the path of the microcatheter, yet is rigid enough to provide structural support so that the deployment apparatus does not inadvertently kink or otherwise become damaged.

In performing endovascular embolization procedures, it may be required to partially or fully withdraw the deployment apparatus from the microcatheter after the sheath has been removed and discarded. For example, if the deployment apparatus feels stressed or is otherwise not positioned properly, it may be desirable to withdraw and reposition the deployment apparatus and the accompanying embolization member(s). However, if the sheath has already been removed from the deployment apparatus in order to permit the deployment apparatus to be inserted into the microcatheter, it is typically necessary to discard the entire deployment apparatus and accompanying embolization member(s) and to replace them with a new deployment apparatus and the accompanying embolization member(s) housed within a new protective sheath. The discarding of a useable deployment apparatus and the accompanying embolization member(s) simply because they cannot be re-inserted into their protective sheath constitutes a significant waste of money and resources. In addition, typical vascular embolization procedures require extreme skill and time, and having to completely remove and reinsert a new deployment structure into a microcatheter results in a significant waste of time, which may negatively affect patient outcome.

Thus, there remains a need in the art for the development of new embolization systems wherein the deployment apparatus and the accompanying embolization member(s) may be resheathed, thereby enabling the deployment apparatus and the accompanying embolization member(s) to be reinserted and repositioned during the performance of a transluminal embolization procedure.

SUMMARY OF THE INVENTION

The present invention provides resheathing apparatus useable to resheath an elongate member such as but not limited to a tube, catheter, embolization member deployment apparatus or other elongate structure. The resheathing apparatus may comprise a guide that has one or more lumens extending from the proximal end to the distal end of the guide. The guide also may have a branch extending away from the lumen of the guide. The branch is structured to fit in a sheath that may be disposed around the deployment structure. The branch is oriented to direct the sheath on to, or off of, the deployment structure depending on whether the deployment structure is to be resheathed, or desheathed, respectively. The resheathing apparatus may also comprise a guide tube disposed over the branch of the guide to facilitate the movement of the sheath over the branch of the guide and over the deployment structure.

Further in accordance with the invention, there is provided an endovascular apparatus for insertion through a catheter positioned in a patient's vasculature. Such endovascular apparatus may comprise a) an elongate, flexible member; b) a sheath removably disposed over at least a portion of the elongate flexible member and c) a resheathing component disposed around the sheath and the elongate, flexible member. The elongate, flexible member may have a proximal end and a distal end, and may be structured to be slidably disposed within a tube or catheter. In certain embodiments of the invention, the catheter may be a microcatheter. The elongate, flexible member may comprise a tube having a lumen extending longitudinally therethrough. Or, the elongate, flexible member may be solid. Such endovascular device may further comprise one or more releasable articles, such as implantable devices, embolic members or embolization coils, drug delivery implants, etc. positioned on or attached to the distal end of the elongate, flexible member. Such releasable article(s) may be released or disconnected from the elongate, flexible member when it is desired to sever the connection between the elongate, flexible member and the releasable article(s). Any suitable type of frangible, severable or releasable connection may be used. For example, the releasable article(s) may be released by injecting or pressurizing fluid within a lumen of the elongate, flexible member or by causing the releasable connection to melt, thermally degrade, dissolve or otherwise separate.

Still further in accordance with the invention, the sheath component of the endovascular apparatus may have a proximal end, a distal end and a slit that extends from the proximal end toward the distal end. In some embodiments, such slit may extends extend over the majority of the length of the sheath, but not all the way to the distal end. In other embodiments, the slit may extend the entire length of the sheath, all the way to its distal end.

Still further in accordance with the invention, the resheathing component of the foregoing endovascular apparatus may be structured to urge or direct the sheath over the deployment tube, and such resheathing component may comprise a guide member that has a lumen extending from its proximal end to its distal end. Such guide member has a first portion structured to receive the elongate, flexible member and a second portion or branch that is structured to receive the sheath. The second portion or branch diverges or extends away from the lumen at one end of the guide member. The second portion or branch of the resheathing apparatus may extend away from the lumen at the proximal end of the guide member.

Still further in accordance with the invention, the resheathing component may also comprise a guide tube disposed around the branch of the guide member. The second portion or branch of the guide member may be structured to separate or widen a slit in the sheath so that the inner diameter of the sheath becomes greater than the outer diameter of the elongate, flexible tube. Furthermore, movement of the resheathing component along the length of the elongate, flexible member may cause either desheathing or resheathing of the elongate, flexible member, depending on the particular direction in which the resheathing component and elongate flexible member move relative to one another.

Still further in accordance with the invention, there is provided an apparatus for endovascular embolization. Such endovascular embolization apparatus my be configured for insertion through a microcatheter (or other catheter) positioned in the vasculature of a human or veterinary patient and may comprise a) an elongate, flexible deployment member, b) an embolic device releasably attached to the distal end of the deployment tube, c) a sheath removably disposed around the deployment tube, said sheath having a slit extending from its proximal end toward its distal end and d) a resheathing apparatus configured and constructed to reposition the sheath around the deployment member after a portion of the sheath has been removed from the deployment member. The deployment member may be tubular or solid. The resheathing apparatus may have a first lumen structured to receive the deployment tube, and a branch portion that diverges from or extends away from the first lumen. The branch portion is configured to interact with the sheath in such a manner as to cause the elongate deployment member to become separated from the sheath as the elongate deployment member is advanced in the distal direction and to cause the elongate deployment member to become reinserted within the lumen of the sheath as the deployment member i9s withdrawn in the proximal direction. The foregoing apparatus may also comprise a guide tube having a slit between the proximal end and the distal end, and disposed over the branch of the guide and structured to receive the sheath.

Still further in accordance with the invention, there is provided an apparatus for directing a sheath or covering around an elongate member as the elongate member is moved along its longitudinal axis. This apparatus may comprise a guide having a proximal end with a single aperture, and a distal end with at least one aperture, and at least one lumen connecting the apertures, the at least one lumen structured to receive the tube, and a branch extending away from the at least one lumen at an orientation that directs the sheath around a portion of the tube extending from the distal end of the guide. The apparatus may also comprise a guide tube having a slit for receiving the branch of the guide between the proximal end and the distal end of the guide tube. The inner diameter of the guide tube may be greater than the outer diameter of the branch of the guide. The proximal and distal ends of the guide tube may extend beyond the proximal and distal ends of the guide, respectively. The guide may also have a handle for controlling the position of the guide with respect to the deployment tube.

Still further in accordance with the invention, there is provided an endovascular catheter device comprising a catheter having an axial lumen and dimensioned for insertion into a patient's vasculature; an elongate, flexible tube dimensioned for insertion through the axial lumen of the catheter; a sheath having a slit along the length of the sheath, disposed around the elongate, flexible tube; and an apparatus disposed around the sheath and the deployment tube, the apparatus is structured to urge the sheath on to the elongate flexible tube. The catheter may be a microcatheter. The device may also comprise an embolic device releasably attached to the distal end of the elongate flexible tube. The apparatus of the device may comprise a guide having a lumen extending from the proximal end to the distal end, and a branch oriented away from the lumen at one end of the guide so that the sheath may be slidably directed on to the elongate, flexible tube. The apparatus may also comprise a guide tube disposed around the branch of the guide. The guide tube may be structured to receive the sheath and direct the sheath over the branch of the guide.

Still further in accordance with the invention, there are provided methods for resheathing a tube that is insertable through an endovascular catheter or other tubular member. Such methods may comprise the steps of: (a) providing an assembly, which comprises an elongate, flexible tube that is insertable through an endovascular catheter; a flexible sheath having a portion that is positioned on the tube and a portion that has been removed from the tube, the sheath having a slit extending the majority of the length of the sheath; and a resheathing apparatus positioned on the elongate flexible tube and the flexible sheath; and (b) urging the resheathing apparatus along the length of the elongate, flexible tube so that the portion of the flexible sheath that has been removed from the tube is directed on to the elongate, flexible tube near the portion of the flexible sheath that is positioned on the elongate, flexible tube. The resheathing apparatus may comprise a guide that has a lumen extending from the proximal end to the distal end and is structured to receive the elongate, flexible tube; and a branch oriented away from the lumen that is structured to fit in the flexible sheath, and is oriented to direct the sheath over the elongate, flexible tube. The resheathing apparatus may also comprise a guide tube disposed around the branch of the guide. The flexible sheath may be urged through the guide tube before the sheath is positioned on the elongate flexible tube. The branch of the guide may be oriented away from the lumen of the guide at the proximal end of the guide so that urging the resheathing apparatus towards the proximal end of the elongate flexible tube causes the elongate flexible tube to be resheathed.

Still further aspects and elements of the present invention will become apparent to those skilled in the art upon reading and considering the detailed descriptions of examples set forth herebelow and in the accompanying drawings.

BRIEF DESCRIPTION OF THE DRAWINGS

FIG. 1 is a plan view of a microcatheter system used in vascular embolization.

FIG. 1A is a magnified perspective view of boxed region 1A shown in FIG. 1 depicting a resheathing apparatus disposed over elements of the microcatheter system of FIG. 1.

FIG. 2 is a perspective view of a guide tube of the resheathing apparatus of FIG. 1A.

FIG. 3A is a perspective view of a guide usable with the resheathing apparatus of FIG. 1A.

FIG. 3B is a perspective view of another guide usable with the resheathing apparatus of FIG. 1A.

FIG. 5 is a sectional view along line 5—5 of FIG. 1A.

DETAILED DESCRIPTION OF SPECIFIC EMBODIMENTS

The following detailed description is provided for the purpose of describing only certain embodiments or examples of the invention and is not intended to describe all possible embodiments and examples of the invention. For example, although the description herein describes a resheathing apparatus used with microcatheter system for endovascular embolization in human and/or veterinary patients, the resheathing apparatus may be used with any catheter system employing a device that may be sheathed prior to the insertion of the device into a catheter-like apparatus.

Figure 1C:
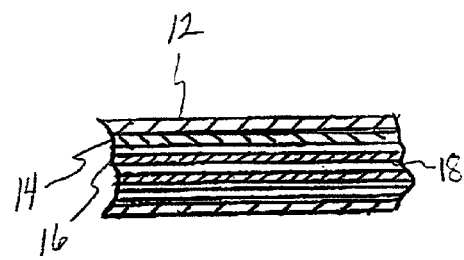
FIG. 1C is a magnified sectional view along line 1C—1C of FIG. 1.
Figure 1B:
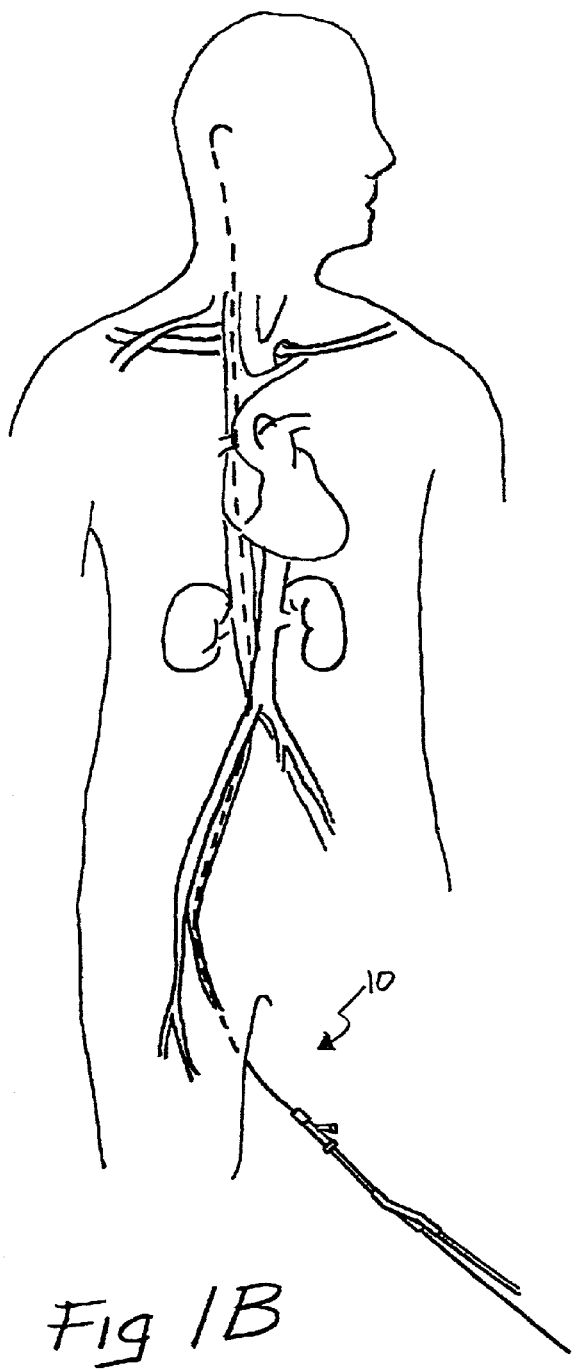
FIG. 1B is a schematic representation of a microcatheter system inserted into a patient's vasculature.

Referring to the figures, and in particular FIG. 1, an example of a microcatheter system 10 is illustrated. As illustrated, microcatheter system 10 comprises guide catheter 12 inserted in a patient's vasculature V. Guide catheter 12 may be inserted into a patient via any appropriate route depending on the location of the site needing treatment. In embodiments of the invention where an aneurysm is located in the patient's brain, which for purposes of the disclosure herein includes the hindbrain regions, such as the brain stem, midbrain regions, and forebrain regions, the guide catheter may be inserted into the patient so that the distal end of the guide catheter is proximate the vertebral or carotid arteries. As illustrated in FIG. 1B, a microcatheter system 10 is illustrated as having been inserted through the femoral artery, through the aorta, and into a patient's brain vasculature. In certain embodiments, it may also be conceivable to insert a catheter directly into a patient's vertebral or carotid arteries.

Referring again to FIG. 1, microcatheter 14 may be inserted through a longitudinal lumen of guide catheter 12. Microcatheter 14 is structured so that the outer diameter of microcatheter 14 is less than the inner diameter of guide catheter 12. Microcatheters may range in outer diameter from $\frac{1}{21,000}$ to $\frac{1}{31,000}$ of an inch, or in other words, the microcatheters may be 10- to 18-type microcatheters. Microcatheter 14 comprises a flexible elongated hollow body fabricated from a biocompatible material, such as a biocompatible metal or plastic. As is conventionally practiced, the distal end of microcatheter 14 may be inserted and directed to a target site T by utilizing a guide wire disposed within a longitudinal lumen of the microcatheter (not shown). The guide wire and/or the microcatheter may have one or more radiopaque regions to facilitate visualization of the guidewire and/or microcatheter, as they progress through the guide catheter and patient's vasculature. Once the microcatheter has been inserted to the target site, such as at an aneurysm site, the guide wire may be retracted and removed from the microcatheter.

The proximal end of microcatheter 14 may be connected to a valve, such as a rotating hemostatic Y valve (RHV). The RHV has a hub for receiving a syringe, and a hub for receiving a deployment tube, as discussed herein. RHVs are conventionally known and publicly available.

As illustrated in FIG. 1, microcatheter system 10 also comprises a deployment tube 16 structured to be inserted through microcatheter 14 to the target site within the patient. Deployment tube 16 is an elongate, flexible tube. In the illustrated embodiment of the invention, deployment tube 16 has a lumen 18 (see FIG. 1A) extending from the proximal end to the distal end of the deployment tube. In other embodiments of the invention, deployment tube 16 may be solid, e.g., it may not have a lumen extending from the proximal end to the distal end. One example of a solid deployment tube is a wire that is attached to a electrical heat-releasable microcoil, such as the Guglielmi Detachable Coil (GDC), as is understood by persons skilled in the art. Deployment tube 16 includes an embolic device 20 releasably attached at, or near, the distal end of the deployment tube. In the illustrated embodiment, embolic device 20 is a microcoil. Examples of embolic devices useful with the microcatheter system of the present invention include, but are not limited to, those disclosed in commonly owned U.S. Pat. Nos. 6,015,424; 6,165,193; and 6,299,619 B1, the contents of which in their entireties are hereby incorporated by reference.

Deployment tube 16 may be inserted or urged into microcatheter 14 so that embolic device 20 may be positioned or otherwise placed in, or near, an aneurysm. Confirmation of the position of embolic device can be obtained using conventional methodology, such as by monitoring the position of the radiopaque material of the embolic device or deployment tube. When embolic device 20 is suitably positioned, as determined by the practicing physician, embolic device 20 may be released from deployment tube 16. With reference to the illustrated embodiment, embolic device 20 may be released by applying pressure through longitudinal lumen 18 of deployment tube 16. In embodiments of the invention employing solid deployment tubes, as described supra, embolic device may be released by passing electrical current through the deployment tube so as to heat the distal end of the deployment tube, and cause the attachment means of embolic device 20 to deployment tube 16 to melt.

After release of embolic device 20, deployment tube 16 may be retracted and withdrawn from microcatheter 14. One or more additional deployment tubes containing embolic devices may be inserted into microcatheter 14, as needed, to sufficiently pack the aneurysm.

As understood, deployment tube 16 is a flexible device that may benefit from structural support. Structural support may facilitate the insertion of deployment tube 16 into microcatheter 14. For example, a structural support member may help reduce, even prevent, the likelihood of deployment tube 16 from being forced into a configuration that may damage the deployment tube. In addition, a structural support may be provided to protect deployment tube 16 from becoming damaged before it is inserted into microcatheter 14.

Referring to the illustrated embodiment of the invention, sheath 22 may be provided around deployment tube 16 to act as a structural support for deployment tube 16. Sheath 22 may extend the entire length of deployment tube 16, for example, from the proximal end to the distal end of the deployment tube. In addition, sheath 22 may extend less than the entire length of the deployment tube. Sheath 22 preferably extends along a length of deployment tube 16 so as to provide structural support and protection to deployment tube 16, as described supra. Sheath 22 may also be made of a suitably flexible material to permit deployment tube 16 to bend as required in order to be positioned at a target site without damage, such as extreme bending or kinking. However, sheath 22 should be somewhat rigid to provide the support and protection, as herein described. For example, sheath 22 may be made of a soft plastic or rubber material. One example of a suitable sheath material is silicone. Sheath 22, as illustrated (see FIG. 1A), may have a slit 24 extending the length of sheath. For example, slit 24 may extend the entire length of the sheath, i.e., from the proximal end of sheath 22 to the distal end. In another example, slit 24 may extend a majority of the length of the sheath, i.e., greater than 50% of the length of the sheath. In the illustrated embodiment, slit 24 of sheath 22 extends from the proximal end of the sheath to approximately the distal end of sheath 22. For example, slit 24 may extend to about one inch from the distal end of sheath 22. The specific distance from the distal end is not to be construed as delimiting of the invention, and in only to be construed as one specific example.

Due to the structural configuration of microcatheter 14, and the structural configuration of deployment tube 16, sheath 22 may not be insertable into microcatheter 14. For example, the combined outer diameter of deployment tube 16 and sheath 22 may be greater than the inner diameter of microcatheter 14. Accordingly, as deployment tube 16 is inserted into microcatheter 14, it may be necessary to withdraw sheath 22 so as to permit the insertion of deployment tube 16 into the lumen of microcatheter 14. For example, the distal end of deployment tube 16 having the sheath at its distal end may be inserted into the RHV so that it abuts the lumen of microcatheter 14. Subsequently, the proximal end of sheath 22 may be pulled proximally and deployment tube 16 may be pushed into the lumen of microcatheter 14.

Referring again to the figures, sheath 22 may be withdrawn from deployment tube 16 by "peeling" sheath 22 away from deployment tube 16 (e.g., see FIG. 1A). The peeling away of sheath 22 from deployment tube 16 may be accomplished by the actions of resheathing apparatus 30. As illustrated in FIG. 1A, resheathing apparatus 30 comprises a guide 32 and a guide tube 42. However, resheathing apparatus may comprise guide 32 without guide tube 42. Resheathing apparatus 30 is disposed on deployment tube 16 so that deployment tube 16 may be resheathed, as described infra. In addition, resheathing apparatus 30 may also be used to peel away, or otherwise remove or withdraw, sheath 22 from deployment tube 16. For example, resheathing apparatus 30 may act to widen slit 24 and urge sheath 22 away from deployment tube 16 as sheath 16 is pulled proximally (i.e., to the left as depicted in FIG. 1A), or as deployment tube 16 is pushed distally (i.e., to the right as depicted in FIG. 1A).

Referring to the illustrated embodiment of resheathing apparatus 30 shown in FIG. 1A, guide 32 has a proximal end and a distal end, and has a lumen 34 extending from the proximal end to the distal end. Lumen 34 is structured to slidably receive deployment tube 16. For example, the diameter of lumen 34 is greater than the outer diameter of deployment tube 16 so that deployment tube 16 may slide within lumen 34. Guide 32 also has a branch 36 extending away from lumen 34. In the illustrated embodiment, branch 36 extends away from one end of lumen 34, such as the proximal end of lumen 34. Branch 36 is illustrated as extending from lumen 34 and creating an angle of approximately 30 degrees. Although the specific angle may not be critical to practice the invention, branch 36 should be at an angle that provides relatively easy removal (and resheathing) of sheath 22 over deployment tube 16. Branch 36 may be relatively blunt at the proximal end 35 to facilitate penetration of branch 36 into the lumen of sheath 22. Guide 32 may be made of any suitably rigid material, including plastics and metals, such as stainless steel. The material of guide 32 should be rigid enough to direct the application or removal of sheath 22 over deployment tube 16, and should be able to be sterilized. Guide 32 may also have a handle 38 (see FIG. 5) to permit a person to grip guide 32. Handle 38 is shown as extending from guide 32 approximately 180 degrees apart from branch 36.

As further depicted in FIG. 1A, branch 36 of guide 32 may be covered by guide tube 42. Guide tube 42 is shown separate from guide 32 in FIG. 2. Guide tube 42 is an elongate hollow structure, that fits over branch 36. For example, guide tube 42 has a distal end 43, a proximal end 45, and a slit 44 disposed between the proximal and the distal end. Slit 44 is structured to receive branch 36 of guide 32. Accordingly, upon insertion of branch 36 into slit 44, guide 32 and guide tube 42 create a single structure capable of resheathing and desheathing deployment tube 16. In the illustrated embodiment, guide tube 42 may have a length longer than the length of branch 36. The longer length of guide tube 42 may help to facilitate the movement of sheath 22 over branch 36, and may facilitate movement of sheath 22 over deployment tube 16. Guide tube 42 may be made of any type of tubing that is flexible enough to permit insertion of branch 36, yet is rigid enough to direct sheath 22 over branch 36. Suitable materials include rubber or plastic tubing, and one specific example is heat shrink tubing.

Figure 4:
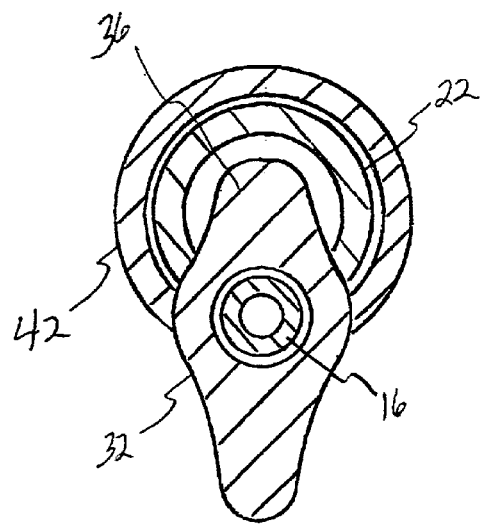
FIG. 4 is a sectional view along line 44 of FIG. 1A.

As indicated above, resheathing apparatus 30 may be used to desheath deployment tube 16 as it is inserted into microcatheter 14. When it is desirable to withdraw deployment tube 16 from microcatheter 14, for example, after a potential problem is encountered in advancing deployment tube 16, or after releasing embolic device 18, it may be desirable to resheath deployment tube 16. As indicated above, no device of which the inventor is currently aware provides means for resheathing such deployment tubes. Thus, conventional deployment tubes must be discarded after removal from microcatheters. Resheathing of deployment tube 16 may be accomplished by sliding resheathing apparatus 30 proximally along deployment tube 16. Referring to FIG. 1A, movement of resheathing apparatus 30 proximally (i.e., to the left), will cause branch 36 of guide 32 to move proximally through sheath 22. As indicated above, the blunt proximal end 35 of branch 36 facilitates the separation of slit 24 and the slidable movement of sheath 22 over branch 36. Near the distal end 33 of branch 36, slit 24 of sheath 22 is sufficiently widened to receive deployment tube 16 extending from the distal end of guide 32. In other words, slit 24 may be opened wider than the outer diameter of deployment tube 16 (see FIG. 4, for example). Accordingly, as sheath 22 slides from distal end 33 of branch 36, slit 24 will assume its natural width (due to the resiliency of the material of sheath 22), and will envelope deployment tube 16 (see FIG. 5, for example). Thus, deployment tube 16 will have been resheathed. Resheathing apparatus 30 may accordingly be slid proximally for the entire length of deployment tube 16 to resheath the entire deployment tube.

In addition, resheathing apparatus 30 may be prevented from desheathing all of deployment tube 16 by providing a sheath 22 that has a slit 24 that does not extend the entire length of the sheath. As will be apparent from the foregoing description, as sheath 22 is pulled proximally along deployment tube 16, sheath 22 is removed from the deployment tube because slit 24 is widened over branch 36 of guide 32 and sheath 22 is directed away from the deployment tube. By providing a non-slit portion of sheath 22 (e.g., at its distal end), sheath 22 will be prevented from moving over branch 36 and away from deployment tube 16. Thus, resheathing apparatus 30 is essentially stopped at the distal end of deployment tube 16.

Although several illustrative examples of means for practicing the invention are described above, these examples are by no means exhaustive of all possible means for practicing the invention. For example, although the foregoing description describes how resheathing apparatus 30 may be used to desheath and resheath deployment tube 16, it may be desirable under certain conditions to desheath deployment tube 16 manually, e.g., by pulling sheath 22 away from deployment tube 16, and subsequently using apparatus 30 to resheath the deployment tube.

In addition, although sheath 22 has a slit 24 in the illustrated embodiments of the invention, other embodiments may provide a sheath that does not have a predefined slit 24. For example, a sheath may be sealed, and may be weakened (e.g., perforated or scribed) along the length of the sheath so that the sheath is effectively secured around deployment tube 16, but that pressure may be used to break the weakened area (e.g., break the perforations or tear the scribe(s)) so as to create a slit in the sheath. Or, the sheath may be provided as a single tubular member without any weakened area (e.g., without perforations or scribes) but it may be made of a suitable material that may be readily torn as necessary to desheath deployment tube 16.

Further, the orientation of resheathing apparatus 30 with respect to deployment tube 16 may be reversed depending upon the particular application of the catheter system, so that branch 36 may be oriented away from lumen 34 of guide 32 at its distal end.

Although guide 32 is illustrated as having one lumen 34 extending therethrough, guide 32 may also be provided with a two or more lumens depending on the number of deployment tube-like structures that may be used. For example, if a catheter system was being used to deliver two or more objects to a target site, a plurality of lumens may be provided in guide 32 to receive each deployment tube-like structure, and each of the deployment structures could be maintained in a single sheath.

What is claimed is:

1. A method of resheathing an elongate apparatus such as a catheter, said method comprising the steps of:
    (a) providing an assembly, which comprises
        an elongate, flexible member;
        a flexible sheath having a portion that is positioned on the elongate member and a portion that has been removed from the elongate member, the sheath having a length and a slit extending the majority of the length of the sheath; and
        a resheathing apparatus that comprises a guide having a proximal end, a distal end, a first portion having a lumen through which the elongate, flexible member is advanceable and a second portion that diverges away from the lumen, said second portion being structured to cause the portion of the sheath that has been removed from the elongate member to become redisposed around the elongate member as the elongate member is advanced in a first direction through the lumen of the guide's first portion; and,
    (b) moving either the elongate flexible member or the guide such that the elongate member advances in the first direction through the lumen of the guide and the second portion of the guide causes the portion of the sheath that had been removed from the elongate member to become redisposed around the elongate member;
        wherein the resheathing apparatus further comprises a guide tube disposed around the second portion of the guide, and the flexible sheath is urged through the guide tube before the sheath is positioned on the elongate flexible member.

2. The method of claim 1, wherein the second portion of the guide is oriented away from the lumen of the guide's first portion at the proximal end of the guide so that urging the resheathing apparatus towards the proximal end of the elongate flexible member causes the elongate flexible member to be resheathed.

* * * * *